United States Patent
Goad

(10) Patent No.: US 9,942,695 B2
(45) Date of Patent: Apr. 10, 2018

(54) SYSTEM, DEVICE, AND METHOD FOR EMERGENCY INFORMATION MANAGEMENT

(71) Applicant: Kevin William Goad, Waldorf, MD (US)

(72) Inventor: Kevin William Goad, Waldorf, MD (US)

(*) Notice: Subject to any disclaimer, the term of this patent is extended or adjusted under 35 U.S.C. 154(b) by 285 days.

(21) Appl. No.: 14/716,745

(22) Filed: May 19, 2015

(65) Prior Publication Data

US 2016/0342700 A1 Nov. 24, 2016

(51) Int. Cl.
| | |
|---|---|
| *G06F 17/30* | (2006.01) |
| *H04W 4/00* | (2018.01) |
| *H04W 4/22* | (2009.01) |
| *G06F 19/00* | (2018.01) |
| *G06Q 50/00* | (2012.01) |

(52) U.S. Cl.
CPC .......... *H04W 4/008* (2013.01); *G06F 19/327* (2013.01); *G06Q 50/00* (2013.01); *H04W 4/22* (2013.01)

(58) Field of Classification Search
CPC .................................................. G06F 19/327
USPC ....................................................... 707/740
See application file for complete search history.

(56) References Cited

U.S. PATENT DOCUMENTS

| | | | | |
|---|---|---|---|---|
| 5,793,882 | A * | 8/1998 | Piatek | A62B 99/00 235/462.15 |
| 7,091,852 | B2 | 8/2006 | Mason et al. | |
| 7,633,387 | B2 | 12/2009 | Carmichael et al. | |
| 8,068,008 | B2 * | 11/2011 | Connell, II | G06Q 30/00 340/5.2 |
| 8,665,087 | B2 | 3/2014 | Greene et al. | |
| 8,666,359 | B2 | 3/2014 | Zhao et al. | |
| 8,698,631 | B1 | 4/2014 | Briese et al. | |
| 8,751,265 | B2 | 6/2014 | Piett et al. | |
| 8,800,877 | B2 * | 8/2014 | Maus | G06K 17/00 235/380 |
| 2013/0115587 | A1 | 5/2013 | Wang et al. | |
| 2014/0002241 | A1 * | 1/2014 | Elghazzawi | H04W 76/007 340/8.1 |

* cited by examiner

*Primary Examiner* — Chelcie Daye
(74) *Attorney, Agent, or Firm* — IDP Patent Services; Olav M. Underdal

(57) ABSTRACT

A system for emergency information management maintains control of emergency information, including medical information, for a list of active emergency responders, and includes some or all of an emergency information database, an emergency information server, emergency information device, emergency information cards, and proximity chips. The emergency information device includes a processor, a non-transitory memory, an input/output, a user manager, a card reader, an information manager, a biometric scanner, a biometric recognizer, a camera, and a face recognizer. The emergency information device can include configurations as a web application and a mobile app, executing on a mobile device. A method for emergency information management includes storing emergency information, registering active emergency responders, and retrieving emergency information.

20 Claims, 6 Drawing Sheets

Emergency Information Server

Emergency Information Data Aggregator

Method for Emergency Information Management

SYSTEM, DEVICE, AND METHOD FOR EMERGENCY INFORMATION MANAGEMENT

CROSS-REFERENCE TO RELATED APPLICATIONS

N/A

FIELD OF THE INVENTION

The present invention relates generally to the field of emergency response management, and more particularly to methods and systems for managing information associated with emergency responders for use during an emergency response.

BACKGROUND OF THE INVENTION

A major concern during emergency operation is to maintain an overview of deployed Fire/EMS personnel and ensure access to safety critical medical information and next of kin contact information.

Currently most Fire/EMS personnel use printed cards with their information printed on the front/back. Some use common access card (CAC) style cards, which have information stored in a chip on the card. Both methods are insecure and costly.

Current methods for managing personnel accountability typically include:
a. When on duty, an emergency responder keeps an ID on his/her fire gear. Such a card is often referred to as a personnel accountability tag, in the emergency services industry;
b. When en route to an incident, the emergency responder places the ID onto a ring in the emergency vehicle, or sometimes there is an accountability officer on site at the emergency scene that collects the IDs. This is to keep track of all personnel entering/exiting the danger area, ensuring no one gets left, lost, or unaccounted for.
c. If an emergency responder is hurt, is missing, or unaccounted for the safety officer will retrieve the corresponding ID. With traditional ID's there is a risk that the ID may be worn out, for example due to environmental exposure, and therefore difficult or impossible to read. Cards that store the information may be damaged or may contain obsolete information. Find their ID from the safety officer, and hopefully the ID isn't too worn out to read.

As such, considering the foregoing, it may be appreciated that there continues to be a need for novel and improved devices and methods for managing accountability of emergency responders during emergency incidents.

SUMMARY OF THE INVENTION

The foregoing needs are met, to a great extent, by the present invention, wherein in aspects of this invention, enhancements are provided to the existing models for emergency information management.

In an aspect a system for system for emergency information management can include:
a) an emergency information database, which stores emergency information;
b) an emergency information server, can store and look up emergency information;
c) an emergency information device, which can retrieve medical information for users from the emergency information server; and
d) a plurality of emergency information cards, such as printed cards, which include a printed unique user;
such that the emergency information device can maintain a list of active emergency responders, which are associated with an active emergency; and
such that the emergency information device can register a user as an active emergency responder.

In an aspect, the system for emergency information management can enhance the safety, scene accountability, and emergency treatment of injured fire/EMS personnel by providing up-to-date user provided medical information to persons, such as a safety officer or incident commander, that need it.

In a related aspect, the system for emergency information management improves on earlier technologies, systems, and methods by not needing a re-print or reprogramming of any ID/Card. Rather than storing any medical/personal information on the card itself, the card contains an identifier that is used to query a web service to retrieve information that can be updated by the user at any time via a web interface or mobile application. In the event of a lost card, the card can be marked as inactive in the system, rendering the card useless to anyone else that finds the card.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. In addition, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
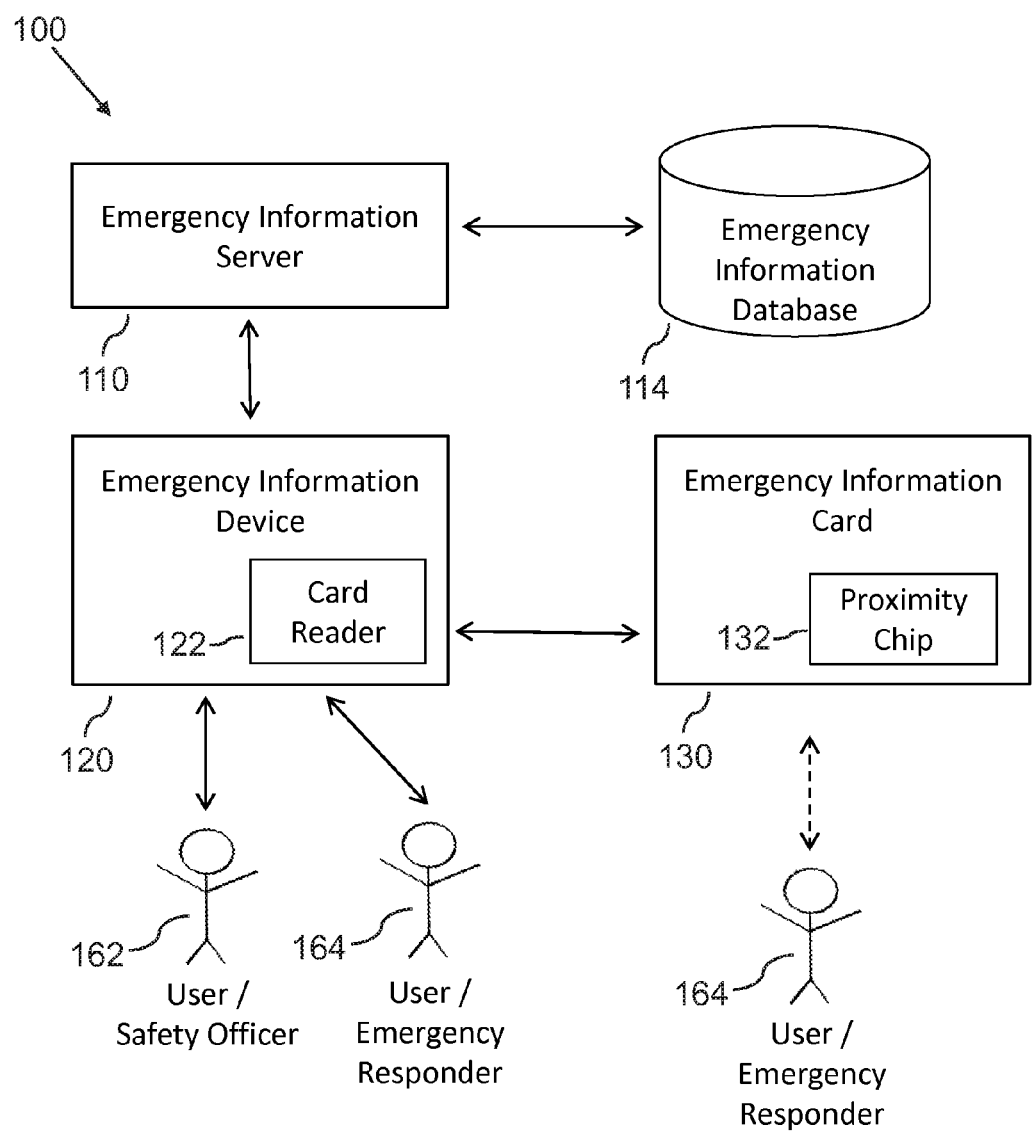
FIG. 1 is a schematic diagram illustrating a system for emergency information management, according to an embodiment of the invention.

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

In the following, we describe the structure of an embodiment of a system for emergency information management 100 with reference to FIG. 1, in such manner that like reference numerals refer to like components throughout; a convention that we shall employ for the remainder of this specification.

In an embodiment a system for system for emergency information management 100 can include:
 a) an emergency information database 114, which stores emergency information for users 164 of the system for emergency information management 100;
 b) an emergency information server 110, which is connected to the emergency information database 114, and can store and look up emergency information for selected users 162;
 c) an emergency information device 120, which is connected to the emergency information server 110, and can retrieve medical information for users 164 from the emergency information server 110; and
 d) at least one emergency information card 130, which can be a printed card, which includes a printed unique user identifier, which is uniquely associated with a user 164;
 wherein the emergency information device 120 maintains a list of active emergency responders, which are associated with an active emergency; and
 wherein the emergency information device 120 can register a user 164 as an active emergency responder by receiving an input of a unique user identifier.

In a related embodiment the emergency information device 120 can register a user 164 as an active emergency responder by receiving an input of a unique user identifier by an emergency manager 162 or a user 164 manually entering this on the emergency information device 120.

In a related embodiment, the system for emergency information management 100, can further include a card reader 122 and the emergency information card 130 can further include a proximity chip 132, which is configured to store and communicate the unique user identifier, such that the emergency information device 120 can register a user 164 as an active emergency responder by receiving an input of a unique user via communication with a card reader 122, which communicates with the proximity chip 132 in the emergency information card 130.

In related embodiments, the unique user identifier can be numeric or alphanumeric.

In a related embodiment, emergency information can include medical information and contact information, including next of kin contact information.

In a related embodiment, a user 162, 164 can enter personal emergency information on the emergency information device 120, via the information manager 312, for storage in the emergency information database 114, in communication via the information repository 210 of the emergency information server 110.

In a related embodiment, an emergency information card 130 can be a proximity card, or prox card, according to well-known methods and technologies for such cards, and can include both active and passive cards. For example, an emergency information card 130 can be a NIMS conforming prox card, i.e. a proximity card, which conforms to the FEMA National Incident Management System standard. Correspondingly, the proximity chip 132 can be the electronics and antenna that are commonly used in proximity cards.

In a related embodiment, an emergency information card 130 can be a NFC enabled smart card. Correspondingly, the proximity chip 132 can be an RFID chip, or another type of near field communicating chip or electronics assembly.

Figure 2:
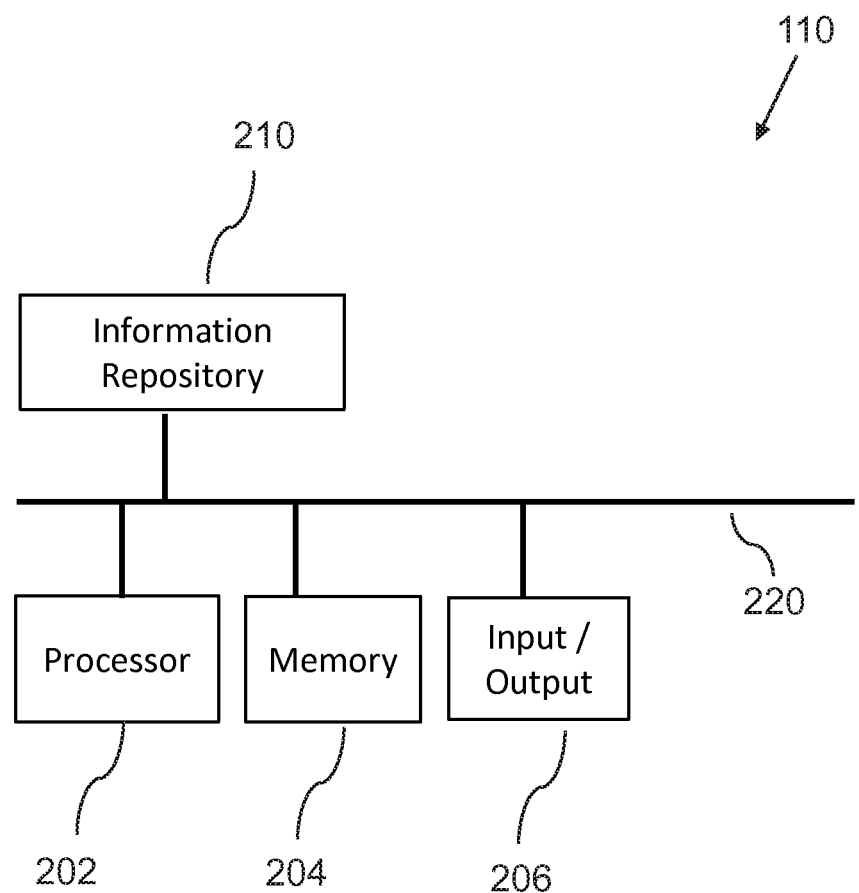
FIG. 2 is a schematic diagram illustrating an emergency information server, according to an embodiment of the invention.

In a related embodiment, as shown in FIG. 2, an emergency information server 110 can include:
 a. A processor 202;
 b. A non-transitory memory 204;
 c. An input/output component 206;
 d. An information repository 210; all connected via
 e. A data bus 220;
 Wherein the information repository 210 is configured to store and look up emergency information for selected users.

Figure 3:
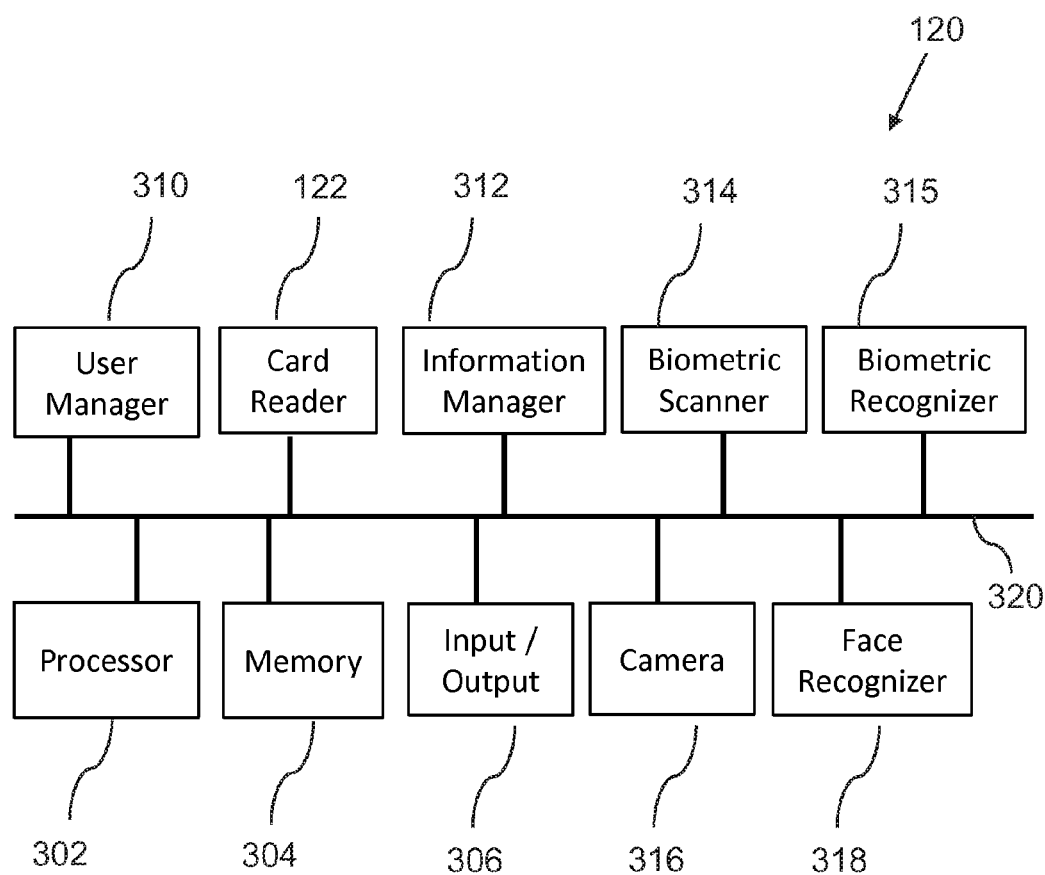
FIG. 3 is a schematic diagram illustrating an emergency information device, according to an embodiment of the invention.

In a related embodiment, as shown in FIG. 3, an emergency information device 120 can include:
 a. A processor 302;
 b. A non-transitory memory 304;
 c. An input/output 306;
 d. An user manager 310;
 e. A card reader 122; and
 f. An information manager 312; all connected via
 g. A data bus 320;
 wherein the information manager 312 can be configured to maintain a list of active emergency responders, which are associated with an active emergency; and
 wherein the information manager 312 can be configured to register a user 164 as an active emergency responder by receiving an input of a unique user identifier.

In related embodiments, the emergency information device 120 can include configurations as:
 a. A web application, executing in a Web browser;
 b. A tablet app, executing on a tablet device, such as for example an Android or iOS tablet device;
 c. A mobile app, executing on a mobile device, such as for example an Android phone or iPhone, or any wearable mobile device;
 d. A desktop application, executing on a personal computer, or similar device;
 e. An embedded application, executing on a processing device, such as for example a smart TV, a game console or other system.

It shall be understood that an executing instance of an embodiment of the system for emergency information management 100, as shown in FIG. 1, can include a plurality of emergency information devices 120, which are each tied to one or more users 162 164.

An executing instance of an embodiment of the system for emergency information management 100, as shown in FIG. 1, can similarly include a plurality of emergency information servers 110.

In a an embodiment, a method for registering a user in the system for emergency information management 100 can include:

a. Creating an account, wherein an emergency responder logs onto SafeOnScene.com and creates an account, and updates his safety information in the system. The safety information can contain addresses, emergency contacts, training records, medical history. The emergency responder can request access to organizations of which he is a member;

b. Requesting a safety ID, wherein the emergency responder requests a safety ID, via a user interface, selecting a sponsoring organization. Typically, the sponsoring organization for the emergency responder will pay service fees for the card;

c. Receiving the safety ID, wherein once approved by the organization, a safety ID is printed to NIMS standards and sent to the emergency responder from a system HQ or a system distribution center.

d. Activating the safety ID, wherein once the emergency responder receives his card, he goes online and activates it. If the card is compromised in transit, there is no risk of information disclosure because the card is unusable until activated, and does not store any information. An activation code can be printed on the card, and be associated with the emergency responder's account, so someone else can't log in without his username/password to activate the card.

In a related embodiment, a user can be a member of multiple organizations, i.e. an emergency responder can volunteer with a volunteer fire department, and be a professional paid fireman with a professional fire department, and use the same account.

In a an embodiment, a method for handling a safety incident in the system for emergency information management 100 can include:

a. Registering active emergency responders, wherein a safety officer, or incident commander, is logged in to the SOS iPad app, and receives emergency information from the apparatus, i.e. fire truck or fire apparatus, swiping them against the card reader;

b. The app goes out to an API, and retrieves the latest information provided by the emergency responder him or herself. It doesn't matter that the ID's are faded, or how long ago it was printed.

c. If the emergency responder is incapacitated, for example suffering a a heart attack (leading cause of firefighter deaths), the Safety officer is immediately able to access all of the emergency responder's information. Up to date information, allergies, including a recent medical operation he had last week, and his recent live-in girlfriend emergency contact are available instantly to the safety officer to provide to EMS, hospital, etc.

In a related embodiment, emergency information cards 130 can be disabled/marked lost or stolen at any time. The card immediately becomes inactive and cannot be used, unless it is reactivated. Since no protected information is stored on the card, no personal information is compromised.

In a related embodiment, as safety officer 162 must be logged in and authorized to access personal information. Any user 164 can swipe the card for basic accountability to access information that is non-confidential, such as information printed on the card, but safety officers 162 have a higher degree of authorization, and can thereby access personal sensitive information.

In a related embodiment, the information manager 312 of the emergency information device 120, can maintain a status of the active emergency responders, wherein the status can include unassigned, dispatched, responding, staging.

In various embodiments, the system for emergency information management 100 can further include a time and attendance system for managing time allocation of users 162 164.

In a related embodiment, the emergency information database 114 can be a secure and encrypted relational database, which cannot be directly accessed by a user.

Figure 4:
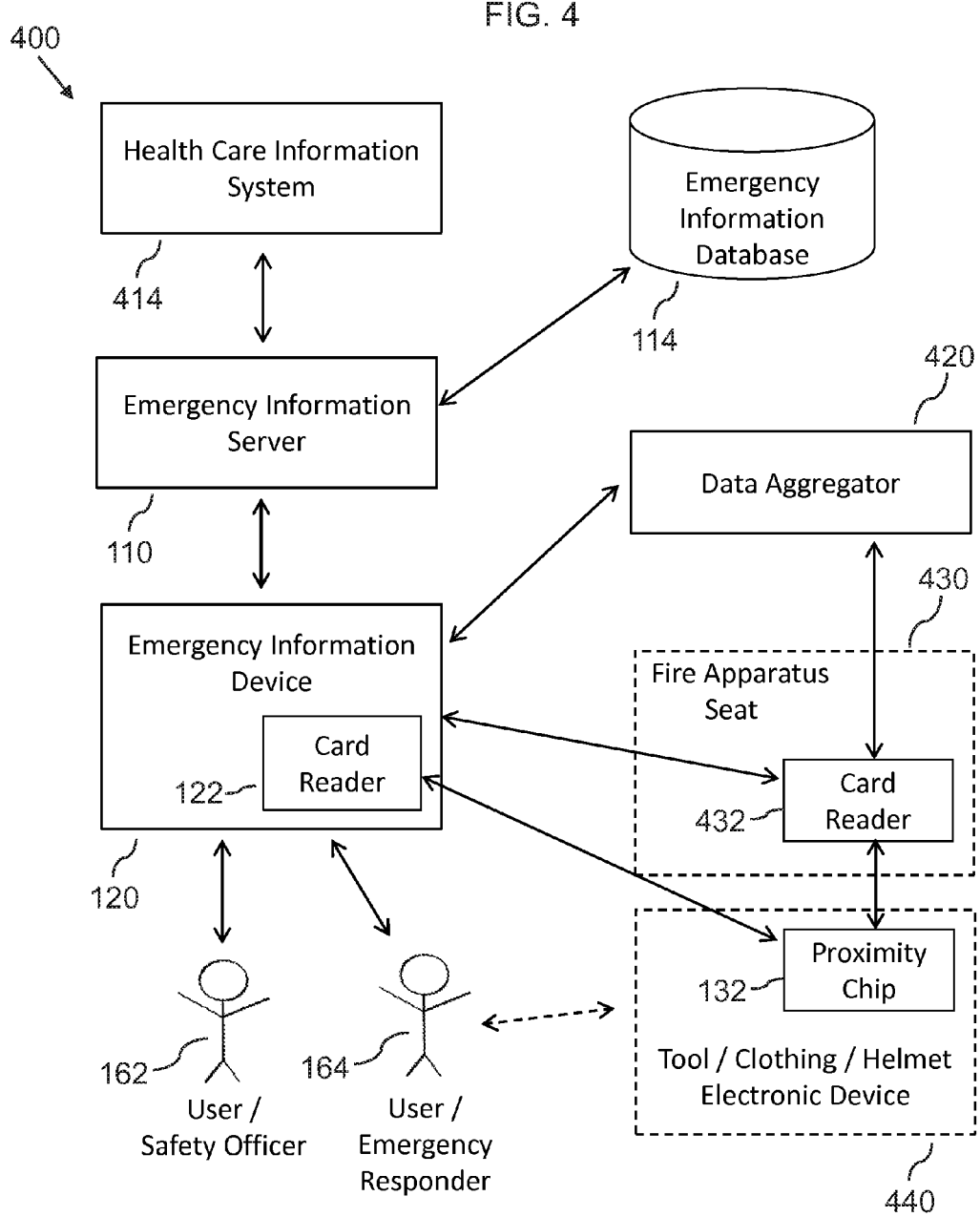
FIG. 4 is a schematic diagram illustrating a system for emergency information management, according to an embodiment of the invention.

In a related embodiment, as shown in FIG. 4, the system for emergency information management 400 can further include:

a. an emergency information data aggregator 420;

wherein the emergency information data aggregator 420 connects to the at least one card reader to receive at least one unique user identifier;

wherein the emergency information device 120 connects with the emergency information data aggregator 420 to receive the at least one unique user identifier.

Figure 5:
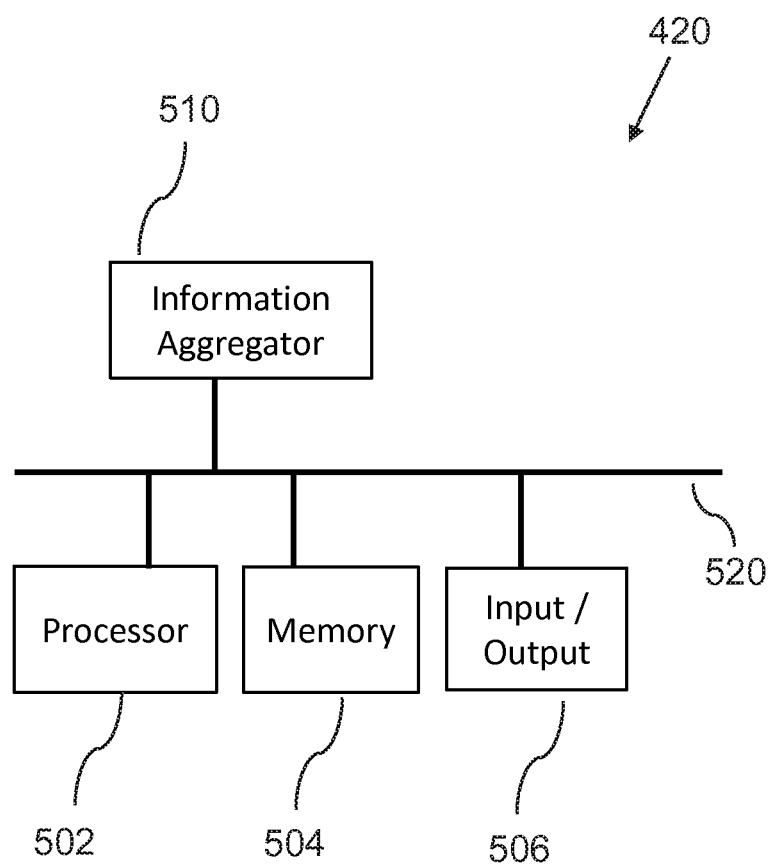
FIG. 5 is a schematic diagram illustrating an emergency information data aggregator, according to an embodiment of the invention.

In a related embodiment, as shown in FIG. 5, an emergency information data aggregator 420 can include:

a. A processor 502;

b. A non-transitory memory 504;

c. An input/output 506; and d. An information aggregator 510; all connected via e. A data bus 520;

wherein the information aggregator 510 connects to the at least one card reader to receive at least one unique user identifier;

wherein the emergency information device 120 connects with the emergency information data aggregator 420 to receive the at least one unique user identifier.

In an embodiment, as shown in FIG. 4, the system for emergency information management 100 can further comprise an emergency information data aggregator 420, wherein a proximity chip 132 can be embedded in:

a. Clothing 440, such as firefighter work shirt;

b. a structural firefighting coat 440;

c. a helmet 440; or d. structural firefighting pants 440;

wherein the emergency information data aggregator 420 connects to at least one card reader 432;

wherein emergency information can be collected by the data aggregator 420, which serves an intermediary device collecting the information, such that the emergency information device 120 can retrieve it via a wireless connection to the emergency information data aggregator 420, such as via Bluetooth, WiFi, cell data connection, or by the mobile device 120 itself using an embedded proximity sensor or wired/wireless scanning device 122 connected to the mobile device 120.

In a related embodiment, a proximity chip 132 can be available to be put in a firefighting or EMS tool 440, such as a flashlight or radio. At the beginning of a shift, an emergency responder 164 can insert their card into a pocket/compartment of the radio 440. In the event of a situation where the firefighter is incapacitated during a smaller incident where accountability/command 162 is not setup, rescuers 164 can retrieve the card. Related to this, emergency information can be collected by the data aggregator 420, which serves an intermediary device collecting the information, such that the emergency information device can retrieve it via a wireless connection, such as Bluetooth, WiFi, cell data connection, or by the mobile device itself using an embedded proximity sensor, or wired/wireless scanning device connected to the device.

In another related embodiment, a proximity chip 132 can be embedded into an electronic device 440, such as a radio. At the beginning of a shift, users 164 would program their ID, or configure their radio to transmit the user identifier for the scanner to read. Instead of the safety officer 162 swiping cards, the safety officer 162 can stand at the edge of a hot zone/emergency incident scene and scan radios. Additionally, the radios can transmit other data as well to the receiver, such as temperature, location, movement, etc. Related to this, emergency information can be collected by the data aggregator 420, which serves an intermediary device collecting the information, such that the emergency information device can retrieve it via a wireless connection, such as Bluetooth, WiFi, cell data connection, or by the mobile device itself using an embedded proximity sensor, or wired/wireless scanning device connected to the device.

In a related embodiment, a plurality of scanner/readers can be embedded in fire apparatus seats 430, such that each scanner/reader establishes individual wireless connection to a proximity chip 132. Each seat 430 would have one or more scanners on the surface, or embedded in them, to scan readers as emergency responders 164 sit in seats 430. Card readers 432 can wirelessly connect to the emergency information device 120 to transmit data.

In a related alternative embodiment, Card readers 432 can connect wired or wirelessly to the data aggregator located in a fire apparatus, which may be another fire apparatus than the one they are located in, and the emergency information device 120 would read the data from the aggregator 420 via a wired or wireless connection.

In a related embodiment, a single long-range card reader can be embedded in a fire apparatus, such that the scanner/reader communicates via a wired or wireless connection to a single data aggregator, which transmits data over a single wired/wireless connection to the emergency information device 120. The scanner would connect wired or wirelessly to the data aggregator located in a fire apparatus, which can be the same fire apparatus or another fire apparatus, and the emergency information device 120 would read the data from the aggregator via a wired or wireless connection.

In a related embodiment, the emergency information device 120 can further include a biometric scanner 314, which for example can include a fingerprint scanner or a retina scanner, such that the information manager 312 is configured to register a user as an active emergency responder by storing an output from the biometric scanner 314 with the unique user identifier, wherein the emergency information manager 312 is configured to identify the user based on matching output from the biometric scanner.

In a related embodiment, the emergency information device 120 can further include a biometric scanner 314 and a biometric recognizer 315, such that the biometric recognizer 315 uses well-known methods for biometric recognition, including pattern matching and picture matching methods, such that the information manager 312 can be configured to register the user as an active emergency responder by further storing a stored biometric scan taken with the biometric scanner 314, wherein the stored biometric scan can be associated with the unique user identifier, such that the biometric recognizer 315 can be configured to identify the unique user id, by matching an instant biometric scan with the stored biometric scan, such that the information manager can receive the input of a unique user identifier from the biometric recognizer 315, which processes the instant biometric scan, which is taken with the biometric scanner 314.

In a related embodiment, the emergency information device 120 can further include a camera 316 and a face recognizer 318, such that the face recognizer 318, uses well-known methods for facial recognition, including pattern matching and picture matching methods, such that the information manager 312 is configured to register the user as an active emergency responder by further storing a stored face photograph taken with the camera 316, wherein the stored face photograph is associated with the unique user identifier, such that the face recognizer 318 is configured to identify the unique user id, by matching an instant face photograph with the stored face photograph, such that the information manager can receive the input of a unique user identifier from the face recognizer 318, which processes the instant face photograph, which is taken with the camera 316.

In a related embodiment, the system for emergency information management 100 can further include a health care information system 414, such as Microsoft HealthVault and other personal health record systems, such that the emergency information server 110 is connected to the health care information system 414, and can store and look up emergency information for selected users 162 in the health care information system 414.

Figure 6:
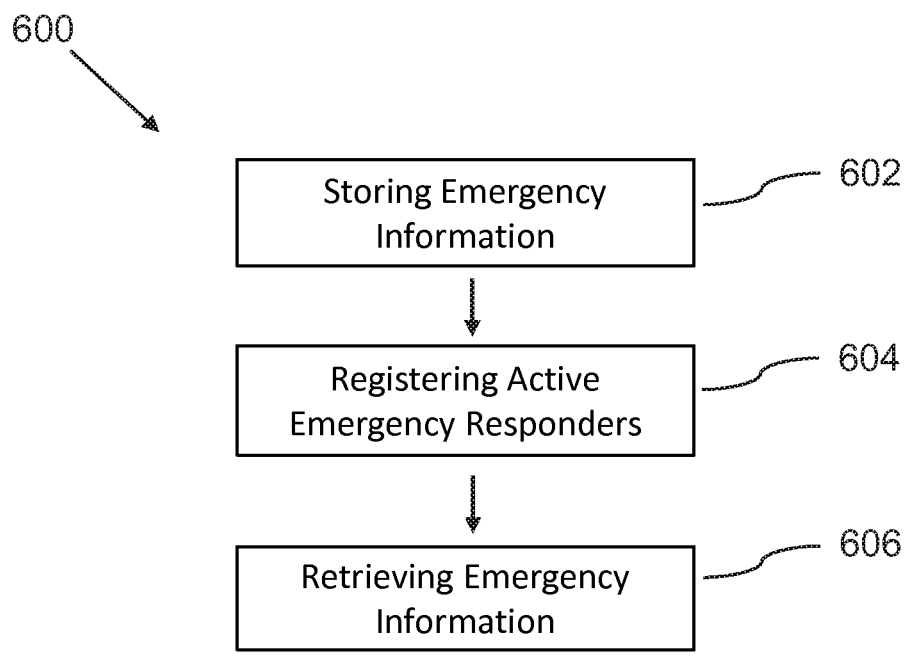
FIG. 6 is a flowchart illustrating steps that may be followed, in accordance with one embodiment of a method or process of emergency information management.

In a related embodiment, as shown in FIG. 6, a method for emergency information management 600 can include:

a. Storing emergency information 602, wherein emergency information is stored by an emergency information server 110;

b. Registering active emergency responders 604, wherein an emergency information device registers active emergency responders by receiving corresponding input of unique user identifiers;

c. Retrieving emergency information 606, wherein emergency information for an active emergency responder is retrieved from the emergency information server 110.

FIGS. 1, 2, 3 and 4 are block diagrams and flowcharts, methods, devices, systems, apparatuses, and computer program products according to various embodiments of the present invention. It shall be understood that each block or step of the block diagram, flowchart and control flow illustrations, and combinations of blocks in the block diagram, flowchart and control flow illustrations, can be implemented by computer program instructions or other means. Although computer program instructions are discussed, an apparatus or system according to the present invention can include other means, such as hardware or some combination of hardware and software, including one or more processors or controllers, for performing the disclosed functions.

In this regard, FIGS. 1, 2, and 3 depict the computer devices of various embodiments, each containing several of the key components of a general-purpose computer by which an embodiment of the present invention may be implemented. Those of ordinary skill in the art will appreciate that a computer can include many components. However, it is not necessary that all of these generally conventional components be shown in order to disclose an illustrative embodiment for practicing the invention. The general-purpose computer can include a processing unit and a system memory, which may include various forms of non-transitory storage media such as random access memory (RAM) and read-only memory (ROM). The computer also may include nonvolatile storage memory, such as a hard disk drive, where additional data can be stored.

FIG. 1 shows a depiction of an embodiment of the system for emergency information management 100, including the emergency information server 110, and the emergency information device 120. In this relation, a server shall be understood to represent a general computing capability that can be physically manifested as one, two, or a plurality of individual physical computing devices, located at one or several physical locations. A server can for example be manifested as a shared computational use of one single desktop computer, a dedicated server, a cluster of rack-mounted physical servers, a datacenter, or network of datacenters, each such datacenter containing a plurality of physical servers, or a computing cloud, such as Amazon EC2 or Microsoft Azure.

It shall be understood that the above-mentioned components of the emergency information server 110 and the emergency information device 120 are to be interpreted in the most general manner.

For example, the processors 202 302 can each respectively include a single physical microprocessor or microcontroller, a cluster of processors, a datacenter or a cluster of datacenters, a computing cloud service, and the like.

In a further example, the non-transitory memory 204 and the non-transitory memory 304 can each respectively include various forms of non-transitory storage media, including random access memory and other forms of dynamic storage, and hard disks, hard disk clusters, cloud storage services, and other forms of long-term storage. Similarly, the input/output 206 and the input/output 306 can each respectively include a plurality of well-known input/output devices, such as screens, keyboards, pointing devices, motion trackers, communication ports, and so forth.

Furthermore, it shall be understood that the emergency information server 110 and the emergency information device 120 can each respectively include a number of other components that are well known in the art of general computer devices, and therefore shall not be further described herein. This can include system access to common functions and hardware, such as for example via operating system layers such as Windows, Linux, and similar operating system software, but can also include configurations wherein application services are executing directly on server hardware or via a hardware abstraction layer other than a complete operating system.

An embodiment of the present invention can also include one or more input or output components, such as a mouse, keyboard, monitor, and the like. A display can be provided for viewing text and graphical data, as well as a user interface to allow a user to request specific operations. Furthermore, an embodiment of the present invention may be connected to one or more remote computers via a network interface. The connection may be over a local area network (LAN) wide area network (WAN), and can include all of the necessary circuitry for such a connection.

In a related embodiment, the emergency information device 120 communicates with the emergency information server 110 over a network, which can include the general Internet, a Wide Area Network or a Local Area Network, or another form of communication network, transmitted on wired or wireless connections. Wireless networks can for example include Ethernet, Wi-Fi, Bluetooth, ZigBee, and NFC. The communication can be transferred via a secure, encrypted communication protocol.

Typically, computer program instructions may be loaded onto the computer or other general-purpose programmable machine to produce a specialized machine, such that the instructions that execute on the computer or other programmable machine create means for implementing the functions specified in the block diagrams, schematic diagrams or flowcharts. Such computer program instructions may also be stored in a computer-readable medium that when loaded into a computer or other programmable machine can direct the machine to function in a particular manner, such that the instructions stored in the computer-readable medium produce an article of manufacture including instruction means that implement the function specified in the block diagrams, schematic diagrams or flowcharts.

In addition, the computer program instructions may be loaded into a computer or other programmable machine to cause a series of operational steps to be performed by the computer or other programmable machine to produce a computer-implemented process, such that the instructions that execute on the computer or other programmable machine provide steps for implementing the functions specified in the block diagram, schematic diagram, flowchart block or step.

Accordingly, blocks or steps of the block diagram, flowchart or control flow illustrations support combinations of means for performing the specified functions, combinations of steps for performing the specified functions and program instruction means for performing the specified functions. It will also be understood that each block or step of the block diagrams, schematic diagrams or flowcharts, as well as combinations of blocks or steps, can be implemented by special purpose hardware-based computer systems, or combinations of special purpose hardware and computer instructions, that perform the specified functions or steps.

As an example, provided for purposes of illustration only, a data input software tool of a search engine application can be a representative means for receiving a query including one or more search terms. Similar software tools of applications, or implementations of embodiments of the present invention, can be means for performing the specified functions. For example, an embodiment of the present invention may include computer software for interfacing a processing element with a user-controlled input device, such as a mouse, keyboard, touch screen display, scanner, or the like. Similarly, an output of an embodiment of the present invention may include, for example, a combination of display software, video card hardware, and display hardware. A processing element may include, for example, a controller or microprocessor, such as a central processing unit (CPU), arithmetic logic unit (ALU), or control unit.

Here has thus been described a multitude of embodiments of the system for system for emergency information management 100 with devices, and methods related thereto, which can be employed in numerous modes of usage.

The many features and advantages of the invention are apparent from the detailed specification, and thus, it is intended by the appended claims to cover all such features and advantages of the invention, which fall within the true spirit and scope of the invention.

For example, alternative embodiments can reconfigure or combine the components of the emergency information server 110 and the emergency information device 120. The components of the emergency information server 110 can be distributed over a plurality of physical, logical, or virtual servers. Parts or all of the components of the emergency information device 120 can be configured to operate in the emergency information server 110, whereby the emergency information device 120 for example can function as a thin client, performing only graphical user interface presentation and input/output functions. Alternatively, parts or all of the components of the emergency information server 110 can be configured to operate in the emergency information device 120. Similarly, the emergency information database 114, can be an integral component of the emergency information server 110.

Many such alternative configurations are readily apparent, and should be considered fully included in this specification and the claims appended hereto. Accordingly, since numerous modifications and variations will readily occur to those skilled in the art, it is not desired to limit the invention to the exact construction and operation illustrated and described, and thus, all suitable modifications and equivalents may be resorted to, falling within the scope of the invention.

What is claimed is:

1. A system for emergency information management, comprising:
    a) an emergency information server, which is configured to store and look up emergency information for a user;
    b) an emergency information device, which is connected to the emergency information server, such that the emergency information device retrieves emergency information for the user from the emergency information server;
    c) at least one card reader;
    d) at least one proximity chip, which is configured to store and communicate the unique user identifier; and
    e) an emergency information data aggregator, comprising:
        a first processor;
        a first non-transitory memory;
        a first input/output; and
        an information aggregator; all connected via
        a first data bus;
    wherein the emergency information device maintains a list of active emergency responders, which are associated with an active emergency; and
    wherein the emergency information device registers the user as an active emergency responder by receiving an input of at least one unique user identifier via communication with the emergency information data aggregator, such that the data aggregator is an intermediary device;
    wherein the information aggregator connects to the at least one card reader to receive the at least one unique user identifier, wherein the at least one card reader communicates with the at least one proximity chip to receive the at least one unique user identifier;
    wherein the emergency information device connects with the emergency information data aggregator to receive the at least one unique user identifier.

2. The system for emergency information management of claim 1, further comprising:
    an emergency information database, which stores emergency information for users of the system for emergency information management;
    wherein the emergency information server is connected to the emergency information database, such that the emergency information server is configured to look up emergency information for the user, via access to the emergency information database.

3. The system for emergency information management of claim 1, further comprising:
    at least one emergency information card, which comprises the unique user identifier.

4. The system for emergency information management of claim 3, wherein the emergency information card is configured such that the unique user identifier is printed on the emergency information card.

5. The system for emergency information management of claim 3,
    wherein the emergency information card further comprises the at least one proximity chip.

6. The system for emergency information management of claim 1, wherein the emergency information comprises medical information and contact information.

7. The system for emergency information management of claim 1, wherein the emergency information server further comprises:
    a. a second processor;
    b. a second non-transitory memory;
    c. a second input/output component;
    d. an information repository; all connected via
    e. a second data bus;
    wherein the information repository is configured to store and look up emergency information for the user.

8. The system for emergency information management of claim 1, wherein the emergency information device further comprises:
    a. a second processor;
    b. a second non-transitory memory;
    c. a second input/output;
    d. the at least one card reader; and
    e. an information manager; all connected via
    f. a second data bus;
    wherein the information manager is configured to maintain a list of active emergency responders, which are associated with an active emergency; and
    wherein the information manager can be configured to register the user as an active emergency responder by receiving an input of a unique user identifier.

9. The system for emergency information management of claim 1, wherein the emergency information device is configured as a mobile app, executing on a mobile device.

10. The system for emergency information management of claim 8, wherein the emergency information device further comprises
    a biometric scanner; and
    a biometric recognizer;
    such that the information manager is configured to register the user as an active emergency responder by further storing a stored biometric scan taken with the biometric scanner, wherein the stored biometric scan is associated with the unique user identifier, such that the biometric recognizer is configured to identify the unique user id, by matching an instant biometric scan with the stored biometric scan, such that the information manager receives the input of a unique user identifier from the biometric recognizer, which is configured to process the instant biometric scan, which is taken with the biometric scanner.

11. The system for emergency information management of claim 8, wherein the emergency information device further comprises
    a. a camera; and
    b. a face recognizer;
    such that the information manager is configured to register the user as an active emergency responder by further storing a stored face photograph taken with the camera, wherein the stored face photograph is associated with the unique user identifier, such that the face recognizer is configured to identify the unique user id, by matching an instant face photograph with the stored face photograph, such that the information manager can receive the input of a unique user identifier from the face recognizer, which is configured to process the instant face photograph, which is taken with the camera.

12. The system for emergency information management of claim 8, further comprising:
a health care information system;
such that the emergency information server is connected to the health care information system, wherein the emergency information server stores and looks up emergency information for the user in the health care information system.

13. A method for emergency information management, comprising:
a. storing emergency information, wherein emergency information is stored by an emergency information server;
b. registering active emergency responders, wherein an emergency information device registers active emergency responders by receiving corresponding input of unique user identifiers via communication with an emergency information data aggregator, such that the data aggregator is an intermediary device; wherein the emergency information data aggregator connects to at least one card reader to receive the unique user identifiers, wherein the at least one card reader communicates with at least one proximity chip to receive the unique user identifiers;
c. retrieving emergency information, wherein emergency information for an active emergency responder is retrieved from the emergency information server; and
d. connecting to the at least one card reader, via an emergency information data aggregator to receive at least one unique user identifier, wherein an emergency information device connects with the emergency information data aggregator to receive the at least one unique user identifier;
wherein the emergency information data aggregator comprises:
a processor;
a non-transitory memory;
an input/output; and
an information aggregator; all connected via a data bus;
wherein the information aggregator connects to the at least one card reader to receive at least one unique user identifier.

14. The method for emergency information management of claim 13, wherein:
b. registering active emergency responders further comprises storing stored biometric scans taken with a biometric scanner, wherein the stored biometric scans are associated with the unique user identifiers, such that a biometric recognizer identifies a unique user id, by matching an instant biometric scan with a stored biometric scan, such that the information manager receives an input of the unique user identifier from the biometric recognizer, by processing the instant biometric scan, which is taken with the biometric scanner.

15. The method for emergency information management of claim 13, wherein:
b. registering active emergency responders further comprises receiving the input of unique user identifiers by storing stored face photographs taken with a camera, wherein the stored face photographs are associated with the unique user identifiers, such that the face recognizer identifies a unique user identifier, by matching an instant face photograph with a stored face photograph, such that the information manager receives an input of the unique user identifier from the face recognizer, by processing the instant face photograph, which is taken with the camera.

16. The method for emergency information management of claim 13, wherein:
c. retrieving emergency information further comprises looking up emergency information for the active emergency responder in a health care information system, in communication with the emergency information server, wherein the emergency information server is connected to the health care information system.

17. A system for emergency information management, comprising:
a. an emergency information server, which is configured to store and look up emergency information for a user;
b. an emergency information device, which is connected to the emergency information server, such that the emergency information device retrieves emergency information for the user from the emergency information server, the emergency information device further comprising an information manager,
wherein the information manager is configured to maintain a list of active emergency responders, which are associated with an active emergency; and
wherein the information manager can be configured to register the user as an active emergency responder by receiving an input of a unique user identifier;
c. a camera; and
d. a face recognizer;
wherein the emergency information device registers the user as an active emergency responder by receiving an input of a unique user identifier;
wherein the information manager is configured to register the user as an active emergency responder by further storing a stored face photograph taken with the camera, wherein the stored face photograph is associated with the unique user identifier, such that the face recognizer is configured to identify the unique user id, by matching an instant face photograph with the stored face photograph, such that the information manager can receive the input of a unique user identifier from the face recognizer, which is configured to process the instant face photograph, which is taken with the camera.

18. The system for emergency information management of claim 17, further comprising:
at least one card reader; and
at least one proximity chip, which is configured to store and communicate the unique user identifier;
such that the emergency information device registers the user as an active emergency responder by receiving an input of at least one unique user identifier via communication with the at least one card reader, which communicates with the proximity chip.

19. The system for emergency information management of claim 17, further comprising:
an emergency information data aggregator;
wherein the emergency information data aggregator connects to the at least one card reader to receive the at least one unique user identifier;
wherein the emergency information device connects with the emergency information data aggregator to receive the at least one unique user identifier.

20. The system for emergency information management of claim 19, wherein the emergency information data aggregator further comprises:
a. a processor;
b. a non-transitory memory;
c. an input/output; and
d. an information aggregator; all connected via
e. a data bus;
wherein the information aggregator connects to the at least one card reader to receive the at least one unique user identifier.

* * * * *